(12) United States Patent
Lee et al.

(10) Patent No.: US 11,510,579 B2
(45) Date of Patent: Nov. 29, 2022

(54) APPARATUS AND METHOD FOR DETERMINING CALIBRATION TIMING FOR BLOOD PRESSURE MEASUREMENT IN ELECTRONIC DEVICE

(71) Applicant: Samsung Electronics Co., Ltd., Gyeonggi-do (KR)

(72) Inventors: Hong Ji Lee, Gyeonggi-do (KR); Tae Han Jeon, Gyeonggi-do (KR); Jong In Park, Gyeonggi-do (KR); Hwan Shim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 432 days.

(21) Appl. No.: 16/240,917

(22) Filed: Jan. 7, 2019

(65) Prior Publication Data

US 2019/0223735 A1    Jul. 25, 2019

(30) Foreign Application Priority Data

Jan. 19, 2018  (KR) .................. 10-2018-0006965
Apr. 27, 2018  (KR) .................. 10-2018-0048875

(51) Int. Cl.
*A61B 5/021* (2006.01)
*A61B 5/02* (2006.01)
(Continued)

(52) U.S. Cl.
CPC ............ *A61B 5/02108* (2013.01); *A61B 5/02* (2013.01); *A61B 5/0295* (2013.01); *A61B 5/742* (2013.01);
(Continued)

(58) Field of Classification Search
CPC ..... A61B 5/02108; A61B 5/02; A61B 5/0295; A61B 5/742; A61B 5/02156; G06F 19/30; H04W 4/022
See application file for complete search history.

(56) References Cited

U.S. PATENT DOCUMENTS 4,669,485 A * 6/1987 Russell .................. A61B 5/021
600/492
9,002,380 B2 4/2015 Sabatelli et al.
(Continued)

FOREIGN PATENT DOCUMENTS

EP    3 130 280 A1    2/2017
JP    2000-116609 A    4/2000
(Continued)

OTHER PUBLICATIONS

International Search Report dated Apr. 8, 2019.
European Search Report dated Jun. 5, 2019.
Korean Office Action dated Oct. 19, 2022.

*Primary Examiner* — Michael R Bloch
(74) *Attorney, Agent, or Firm* — Cha & Reiter, LLC

(57) ABSTRACT

An electronic device includes a sensor, a memory, and a display, and a processor. The processor is configured to determine bio-information and blood pressure information of a user measured through the sensor, determine reliability of calibration of the blood pressure information, based on at least one of elapsed time of the calibration, the bio-information, and the blood pressure information, determine, based on the reliability of the calibration, whether an event associated with the calibration occurs, and display a user interface (UI) to request another calibration, through the display, when the event is determined to have occurred.

9 Claims, 14 Drawing Sheets

(51) Int. Cl.
  *H04W 4/021*    (2018.01)
  *A61B 5/0295*   (2006.01)
  *A61B 5/00*     (2006.01)
  *G16H 10/60*    (2018.01)

(52) U.S. Cl.
  CPC ........... *A61B 5/7475* (2013.01); *H04W 4/022* (2013.01); *A61B 2560/0223* (2013.01); *G16H 10/60* (2018.01)

(56) References Cited

U.S. PATENT DOCUMENTS

| | | |
|---|---|---|
| 9,420,420 B2 | 8/2016 | Sabatelli et al. |
| 9,687,161 B2 | 6/2017 | Sethi et al. |
| 10,045,700 B2 | 8/2018 | Noh et al. |
| 10,058,286 B2 | 8/2018 | Hosaka et al. |
| 10,327,649 B1 * | 6/2019 | Mouradian ........ A61B 5/02416 |
| 2010/0081945 A1 | 4/2010 | Sethi et al. |
| 2013/0274617 A1 | 10/2013 | Hosaka et al. |
| 2013/0331127 A1 | 12/2013 | Sabatelli et al. |
| 2015/0289095 A1 | 10/2015 | Sabatelli et al. |
| 2017/0042433 A1 | 2/2017 | Noh et al. |
| 2017/0172431 A1 | 6/2017 | Kim et al. |

FOREIGN PATENT DOCUMENTS

| | | |
|---|---|---|
| JP | 2007-44203 A | 2/2007 |
| KR | 10-2017-0019189 A | 2/2017 |
| NO | 2013/184990 A1 | 12/2013 |

\* cited by examiner

APPARATUS AND METHOD FOR DETERMINING CALIBRATION TIMING FOR BLOOD PRESSURE MEASUREMENT IN ELECTRONIC DEVICE

CROSS-REFERENCE TO RELATED APPLICATION(S)

This application is based on and claims priority under 35 U.S.C. § 119 to Korean Patent Application No. 10-2018-0006965, filed on Jan. 19, 2018, No. 10-2018-0048875, filed on Apr. 27, 2018 in the Korean Intellectual Property Office, the disclosure of which is incorporated by reference herein its entirety.

BACKGROUND

1. Field

The present disclosure generally relates to an apparatus and a method for determining calibration timing for blood pressure measurement in an electronic device.

2. Description of Related Art

Recently, as smartphones and wearable devices having excellent performance characteristics have become increasingly commonplace, these devices are increasingly used for health monitoring. In particular, attention has been paid to various sensing technologies and services for health monitoring, such as those used for measurement of blood sugar and blood pressure.

Non-invasive methods of measuring blood pressure may include, for example, the auscultation method and the oscillometric method. In both the auscultation method and the oscillometric method, a cuff is attached to an upper-arm of the user, pressure higher than diastolic blood pressure is applied to the arm via the cuff, and then the pressure is slowly reduced while the blood pressure is measured.

Meanwhile, there are other ways to estimate blood pressure without using the cuff (hereinafter referred to as cuffless methods). These methods may include a method that employs pulse transit time (PTT) to estimate the blood pressure (hereinafter referred to as "the PPT method"). In the PPT method, the inverse proportional relationship between the blood pressure and the PTT is used to estimate blood pressure. Another cuffless method is pulse wave analysis (PWA) (hereinafter referred to as "the PWA method"), which analyzes the waveform of a PPG signal that corresponds to the waveform of the blood pressure.

The above information is presented as background information only to assist with an understanding of the present disclosure. No determination has been made, and no assertion is made, as to whether any of the above might be applicable as prior art with regard to the present disclosure.

SUMMARY

In the case of the auscultation method, to accurately measure blood pressure, the technician operating the monitor must be skilled. In the case of the oscillometric method, the monitoring device is an electronic blood pressure monitor that makes it easy and convenient to measure the blood pressure. However, the oscillometric method requires an air pump to push air into the cuff and a motor for actuating the air pump, and therefore the oscillometric monitoring device can be quite bulky. Accordingly, the oscillometric blood pressure monitors lack portability.

In addition, under the PTT method, since electrocardiography (ECG) and photoplethysmogram (PPG) are simultaneously measured, it is difficult to measure blood pressure while the user is not constrained and while the user is unaware that measurement is taking place. Accordingly, the PTT method may not be suitable for mobile devices. In addition, under the PWA method, because blood pressure is estimated based on a single PPG signal, the measurement may not be as accurate as other methods. To compensate for the decrease in accuracy, there is required a procedure (hereinafter, referred to as "calibration") of calibrating a blood pressure value estimated based on the PPG signal to a blood pressure value of the electronic blood pressure monitor by measuring the blood pressure together with the electronic blood pressure periodically as well as in the first stage of the blood pressure measurement. However, since the user cannot know timing (hereinafter, referred to as "calibration timing") of the calibration, the user cannot be relied upon to perform the calibration. But if the blood pressure monitor is not properly calibration, the estimated blood pressure readings may not be accurate.

Aspects of the present disclosure are to address at least the above-mentioned problems and/or disadvantages and to provide at least the advantages described below. Accordingly, an aspect of the present disclosure is to determine when calibration is required and to provide a guide or user interface for the calibration to the user, based on the reliability of the calibration.

In accordance with an aspect of the present disclosure, an electronic device may include a sensor, a memory, a display, and a processor. The processor may be configured to determine bio-information and blood pressure information of a user measured through the sensor, determine reliability of calibration of the blood pressure information, based on at least one of elapsed time of the calibration, the bio-information, and the blood pressure information, determine, based on the reliability of the calibration, whether an event associated with the calibration occurs, and display a user interface (UI) to request another calibration, through the display when the event is determined to have occurred.

In accordance with an aspect of the present disclosure, a method of an electronic device may include determining bio-information and blood pressure information of a user measured through a sensor of the electronic device, determining reliability of calibration of the blood pressure information, based on at least one of elapsed time of the calibration, the bio-information, and the blood pressure information, determining, based on the reliability of the calibration, whether an event associated with the calibration occurs, and displaying a UI to request another calibration, through a display of the electronic device, when the event is determined to have occurred.

In accordance with an aspect of the present disclosure, an electronic device may include a housing, a touchscreen display exposed through a first part of the housing, a photoplethysmogram (PPG) sensor exposed through a second part of the housing and configured to make contact with a portion of a user's body such that blood pressure of the user is measured, a wireless communication circuit disposed inside the housing, a processor disposed inside the housing and operatively connected with the touchscreen display, the PPG sensor, and the wireless communication circuit, and a memory disposed inside the housing, operatively connected with the processor, and storing instructions. When executed, the instructions may cause the processor to receive first data from the PPG sensor for a first duration, to determine a first plurality of parameters from the first data, to determine a first parameter for a first time point, based at least partially on at least two parameters in the first plurality of parameters, to receive second data from the PPG sensor for a second duration, to determine a second plurality of parameters from the second data, to determine a second parameter for a second time point, based at least partially on at least two parameters in the second plurality of parameters, to determine calibration timing based at least partially on the second parameter, and to display information associated with the calibration timing on the touchscreen display.

As described above, according to one or more embodiments of the present disclosure, the electronic device may determine whether an event associated with the calibration occurs, based on the reliability of the calibration. If the event occurs, the electronic device may request the user to calibrate the blood pressure information.

According to embodiments of the present disclosure, the electronic device may provide place information associated with the calibration to the user, based on the reliability of the calibration, thereby allowing the user to conveniently perform the calibration.

In addition, a variety of other features can be directly or indirectly understood through the present disclosure.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

In accompanying drawings, same and similar components will be assigned with same and similar reference numerals.

DETAILED DESCRIPTION

Hereinafter, various embodiments of the present disclosure may be described with reference to accompanying drawings. Accordingly, those of ordinary skill in the art will recognize that various modifications, equivalents, and/or alternatives on the various embodiments described herein can be made without departing from the scope and spirit of the present disclosure.

Figure 1:
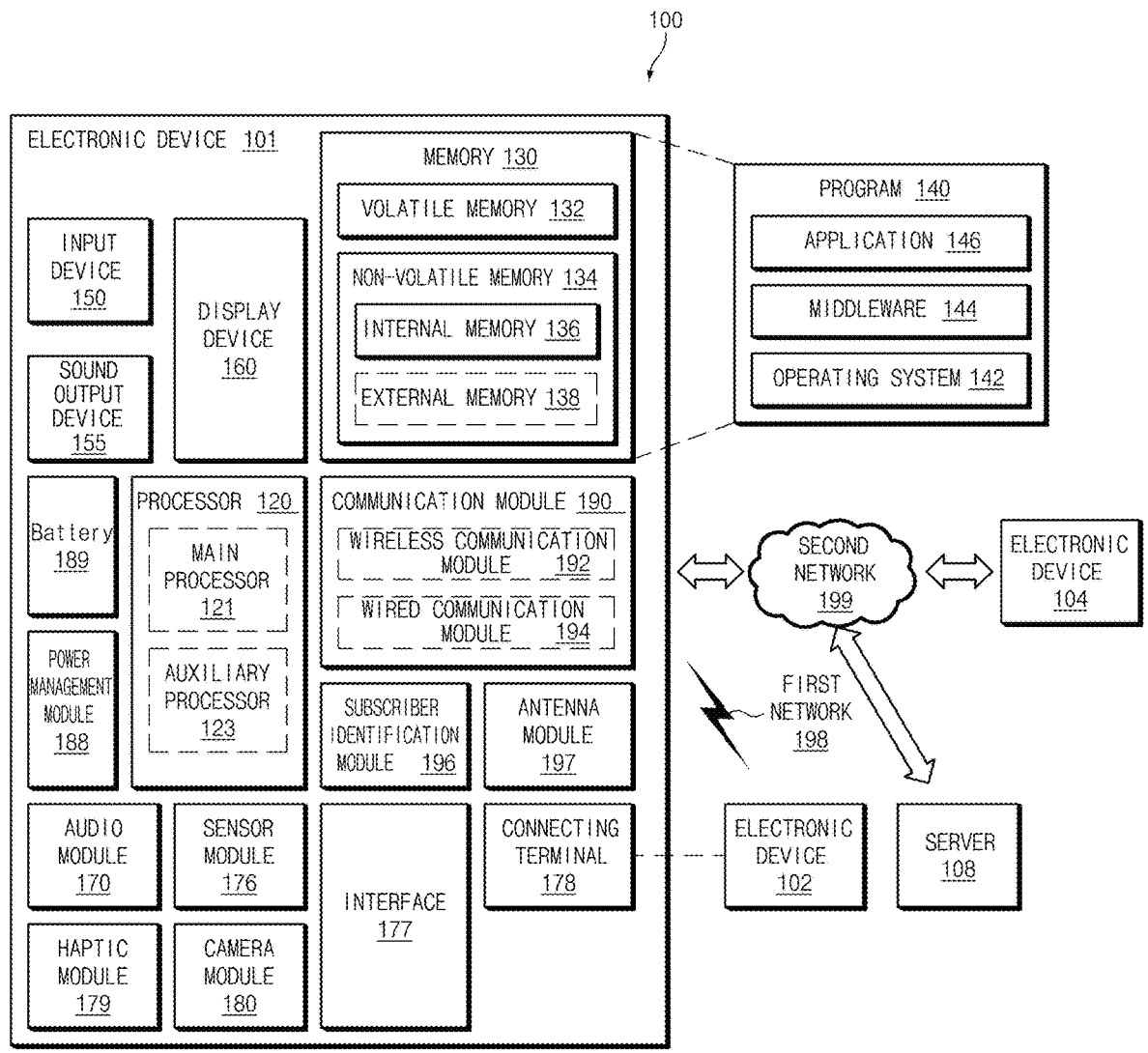
FIG. 1 is a block diagram illustrating an electronic device in a network environment according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
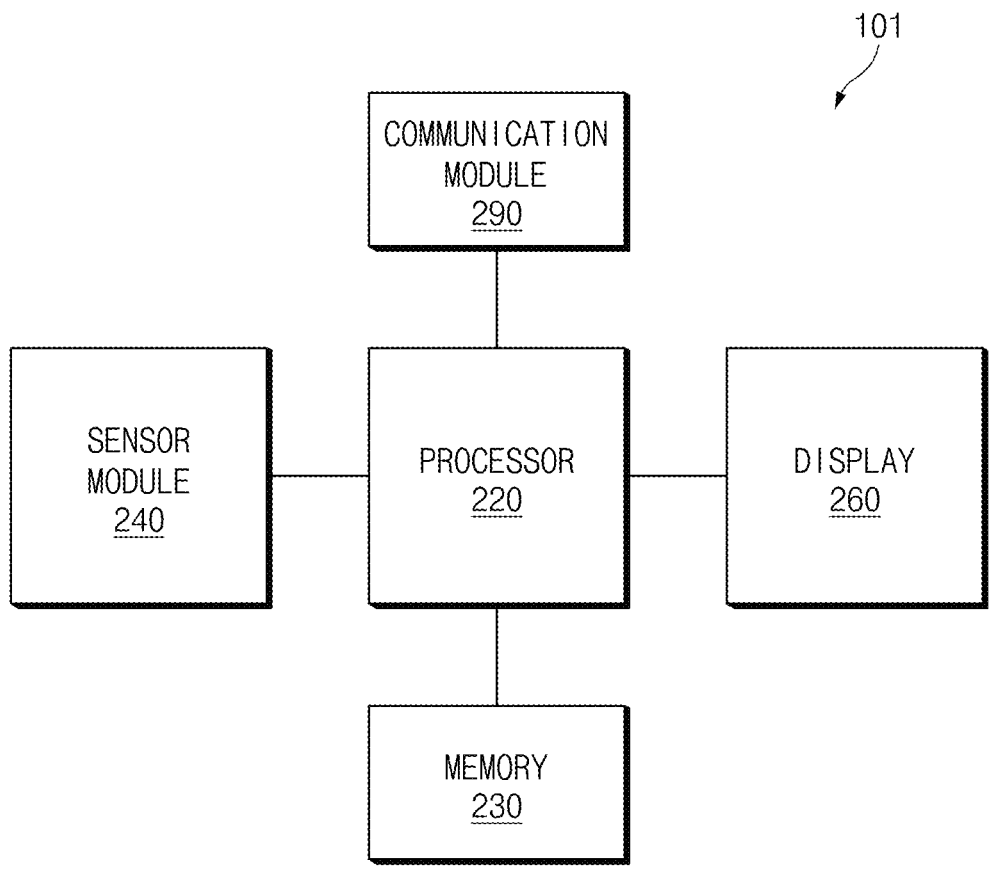
FIG. 2 is a block diagram of an electronic device, according to an embodiment.

FIG. 2 is a block diagram of an electronic device, according to an embodiment.

Referring to FIG. 2, the electronic device 101 may include a processor 220, a memory 230, a sensor module 240, a display 260, and a communication module 290.

According to an embodiment, the electronic device 101 may include a housing (not illustrated) including the processor 220, the memory 230, the sensor module 240, and the display (touchscreen display) 260, and the communication module 290. For example, the display 260 may be exposed through a first part (e.g., a front surface) of the housing and the sensor module 240 may be exposed through a second part (e.g., a rear surface) different from the first part.

According to an embodiment, the sensor module 240 may measure bio-information from a user. The bio-information of the user may include, for example, at least one of information (e.g., body fat or body water) measured through a bioelectrical impedance analyzer (BIA), stress index, exercise amount, blood sugar, sleep duration, exercise time, heartbeat rate information, and blood pressure.

According to an embodiment, the sensor module 240 (e.g., the sensor module 176 of FIG. 1) may make contact with a portion of the user's body and may measure the blood pressure of the user. For example, when the sensor module 240 includes a photoplethysmogram (PPG) sensor, the sensor module 240 may measure, through the optical PPG sensor, the variation in the systolic and diastolic vascular volume caused by the variation in peripheral blood flow. The PPG sensor may measure the variation in the amount of blood inside the blood vessel by using light that is transmitted onto the blood vessel. The PPG sensor may include at least one photodiode (PD) and at least one light emitting diode (LED). The LED may convert electrical energy to light energy. The PD may convert light energy to electrical energy. When light reaches the skin of the user from the LED, a portion of the light may be absorbed into the skin and remaining reflected light may be detected by the PD. The LED may transmit light in one or more wavelengths. For example, the LED may transmit at least one of infrared light and visible light (Red, Blue, and/or Green (RGB) light). The user of the electronic device 101 may touch, with the finger of the user, a portion of the electronic device 101 which includes the PPG sensor and may maintain the touch for a specific time. This input (i.e. long touch) may trigger a blood pressure measurement. In systole, since blood is increased inside the blood vessel, the amount of light detected by the PD may be reduced. In diastole, since blood is decreased inside the blood vessel, the amount of light detected by the PD may be increased. Accordingly, an alternating current (AC) signal may be generated from the PD. The PPG sensor may extract several parameters (e.g., the peak size of the AC signal, a dicrotic notch, the interval between the peaks, or an area ratio of a waveform) by processing the AC signal and may estimate blood pressure based on the extracted parameters. The technology of measuring the blood pressure using the PPG sensor may be referred to as pulse wave analysis (PWA) technology.

For another example, the sensor module 240 may include a PPG sensor, an acceleration sensor, and/or an electrocardiogram (ECG) sensor. The ECG sensor may measure an ECG signal which is an electrical bio-signal generated due to the contraction and relaxation of the heart. The acceleration sensor may measure ballistocardiography (a BCG signal) which relates to the mechanical movement of the heart. The electronic device 101 (e.g., the processor 220) may determine PTT from the heart to a peripheral blood vessel based on a pulse wave measured in the peripheral blood vessel through the PPG sensor, ECG or BCG. The PTT typically varies according to the resistance of the blood vessel. The electronic device 101 may estimate blood pressure information of the user based on a pulse wave velocity (PWV) that is included in the PTT measurement. According to an embodiment, the electronic device 101 may measure both of the pulse wave and the ECG or may measure both the pulse wave and the BCG.

According to an embodiment, the display 260 (e.g., the display device 160 of FIG. 1) may display various user interfaces (UI) to enable user calibration under the control of the processor 220. For example, the display 260 may display place information related to calibration. For another example, the display 260 may display a UI showing the blood pressure of the user based on the calibration. According to an embodiment, the communication module 290 (e.g., the communication module 190 of FIG. 1) may measure the location of the electronic device 101. For example, the communication module 290 may measure the location of the electronic device 101 through a communication module, such as Global Positioning System (GPS), WiFi Positioning System (WPS), global navigation satellite system (GLONASS), or CPS (cyber physical system). In addition, the communication module 290 may be able to measure location through short-range wireless communication modules such as Bluetooth, BLE, WiFi, or NFC. The communication module 290 may communicate with an external device connected with the electronic device 101 under the control of the processor 220. The external electronic device may be, for example, a smartphone, a tablet, a wearable device, a nearable device, a medical device, or a server. According to an embodiment, the electronic device 101 may not include the communication module 290.

According to an embodiment, the processor 220 (e.g., the processor 120 of FIG. 1) may be operatively connected with the sensor module 240, the display 260, the communication module 290, and the memory 230 to perform the overall function of the electronic device 101. The processor 220 may include at least one processor and may be physically divided into a main processor for high-performance processing and an auxiliary processor for low-power processing. For example, the sensor module 240 may be connected with the auxiliary processor to perform continuous health monitoring of the user. Depending on various situations, the processor 220 may perform processing while switching between high-performance processing and low-power processing. The processor 220 may include, for example, an application processor (AP). The processor 220 may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. § 112(f), unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

According to an embodiment, the processor 220 may determine the elapsed time of calibration, bio-information, and/or blood pressure information. According to an embodiment, the elapsed time of the calibration may refer to time elapsed from the previous calibration. The processor 220 may measure the bio-information or the blood pressure information through the sensor module 240 or may store, in the memory 230 (e.g., as part of the application 146), the bio-information or the blood pressure information detected from the user. The bio-information determined through the sensor module 240 may include, for example, at least one of information measured through the BIA, stress index, exercise amount, blood sugar, sleep duration, exercise time, heartbeat rate information, and ECG. The bio-information determined in response to a user input may include, for example, at least one of body mass index (BMI), stress index, blood sugar, heartbeat rate information, and ECG.

According to an embodiment, the processor 220 may determine the reliability of the calibration based on at least one of the elapsed time of the calibration, the bio-information of the user, and the blood pressure information of the user. For example, the processor 220 may apply a weight based on each of the elapsed time, the bio-information, and the blood pressure information.

According to an embodiment, the processor 220 may determine, based on the reliability, whether an event associated with the calibration has occurred. The event associated with the calibration may be a point in time when the calibration expires, hereinafter referred to as the "expiration time point." The expiration time point of the calibration may be determined based on the reliability of the calibration. In another example, the event may be associated with when the reliability of the calibration is less than a specified threshold value. The threshold value may include one or more threshold values.

According to an embodiment, the processor 220 may transmit location information of the electronic device 101 to an external electronic device through the communication module 290 and may receive information associated with the calibration from the external electronic device. According to an embodiment, the processor 220 may display a user interface (UI) to request calibration through the display 260. According to an embodiment, the processor 220 may notify the user that a calibration is requested through sound or vibration. According to an embodiment, the processor 220 may store data in the memory 230 or may read data from the memory 230.

According to an embodiment, the memory 230 (e.g., the memory 130 of FIG. 1) may store instructions used, by the processor 220, to perform operations of the electronic device 101. According to an embodiment, the memory 230 may include information associated with the calibration. The information associated with the calibration may refer to, for example, the elapsed time, the expiration time point, or the reliability of the calibration. According to an embodiment, the memory 230 may store the bio-information and the blood pressure value of the user, and also the location information associated with the calibration.

Figure 3:
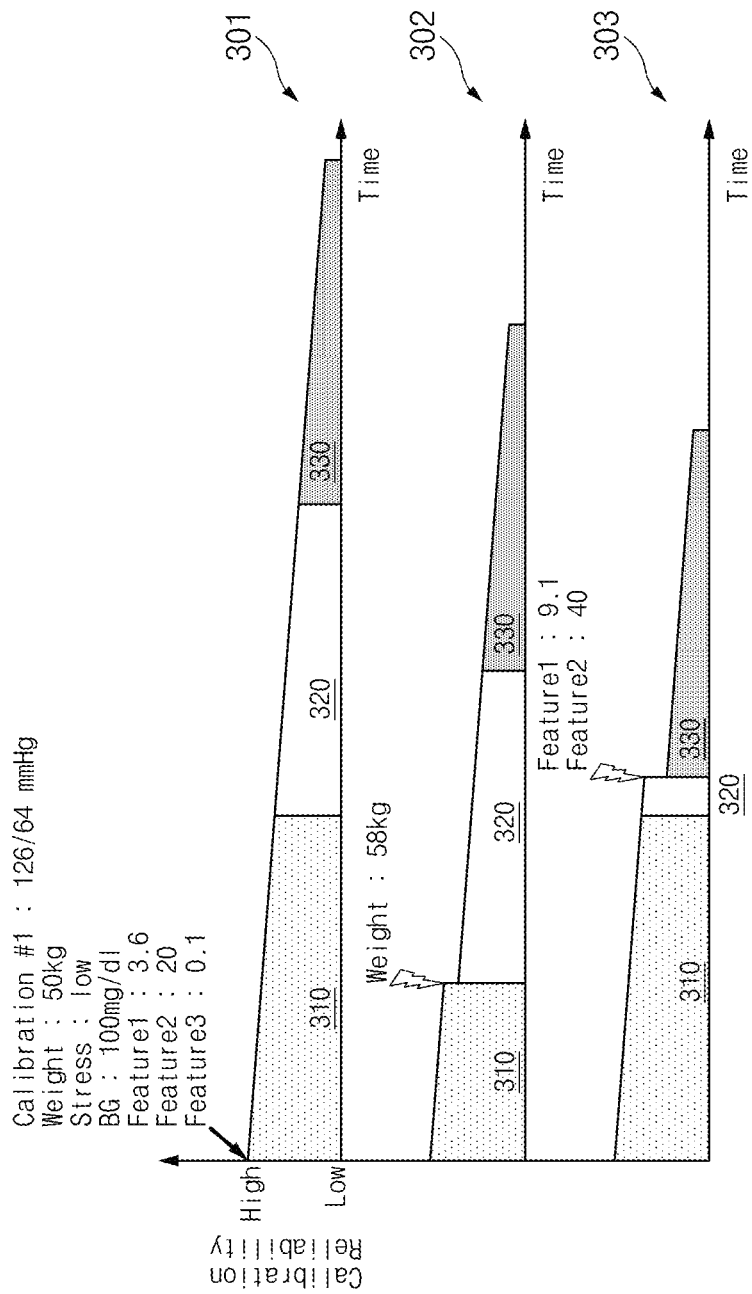
FIG. 3 illustrates graphs representing the reliability of the calibration, according to an embodiment.

FIG. 3 illustrates graphs representing the reliability of the calibration, according to an embodiment.

Referring to FIG. 3, graph 301, graph 302, and graph 303 may show the variation in the reliability of the calibration under different situations. The graphs illustrated in FIG. 3 are provided only for the illustrative purpose, and the reliability of the calibration described in the present disclosure is not limited thereto. In graph 301, graph 302, or graph 303, the vertical axis may represent the reliability of the calibration and the horizontal axis may represent time. The reliability of the calibration may be expressed as, for example, a value between 0 and 1.

According to an embodiment, the reliability of the calibration may consistently decrease over time due to the variation in the bio-information of the user, the variation in the blood pressure information of the user, the variation in the performance of the electronic device 101 or various other reasons over time. The reliability of the calibration may decrease in proportion to time or may abruptly decrease under a specific situation. For example, as illustrated in graph 301, the reliability of the calibration may consistently decrease in proportion to time (e.g., the elapsed time of the calibration). In another example, the electronic device may store a value corresponding to the weight of the user. When that value is abruptly changed from 50 kg to 58 kg as illustrated in graph 302, since one of the factors that causes elevation of blood pressure is increased, the reliability of the calibration may be decreased. The electronic device 101 may be notified of the event where the weight of the user is increased, from an external electronic device (e.g., the electronic device 102, the electronic device 104, or the server 108 of FIG. 1) or receive the event through a user input. In another example, as illustrated in FIG. 3, when a feature point, such as the divergence of blood pressure variability, is detected, the reliability of the calibration may be decreased. The electronic device 101 may measure various factors that affect blood pressure to measure or estimate the reliability of the calibration. Based on these factors, the electronic device 101 may determine the expiration time point of the calibration. The expiration time point of the calibration may be when the reliability becomes 'zero.' When the expiration time point of the calibration comes to pass, the electronic device 101 may provide, for the user, a UI to request calibration.

According to an embodiment, the electronic device 101 may divide the reliability of the calibration into a plurality of stages. For example, referring to graph 301, the electronic device 101 may divide the reliability of the calibration into a higher stage 310 (e.g., in the range of 0.7 to 1), an intermediate stage 320 (e.g., in the range of 0.35 to 0.7), and a lower stage 330 (e.g., in the range of 0 to 0.35). As such, the stage varies with the reliability of the calibration. The electronic device 101 may provide different UIs to the user based on the stages of the reliability, so that the degree of calibration requested corresponds to the current stage of reliability.

Although the description made herein are related to determining the reliability of the calibration for blood pressure, the same principle may be applied to other bio-information. For example, the electronic device 101 may determine the reliability of the calibration of the stress index or cardiovascular health index. According to an embodiment, since the expiration time point of the calibration of the cardiovascular health index is later than the expiration time point of the calibration of blood pressure, and the calibration in the cardiovascular health index is more reliable than the calibration of blood pressure. Accordingly, the electronic device 101 may adaptively manage the expiration time points of various calibrations depending on the types of measured information.

Figure 4A:
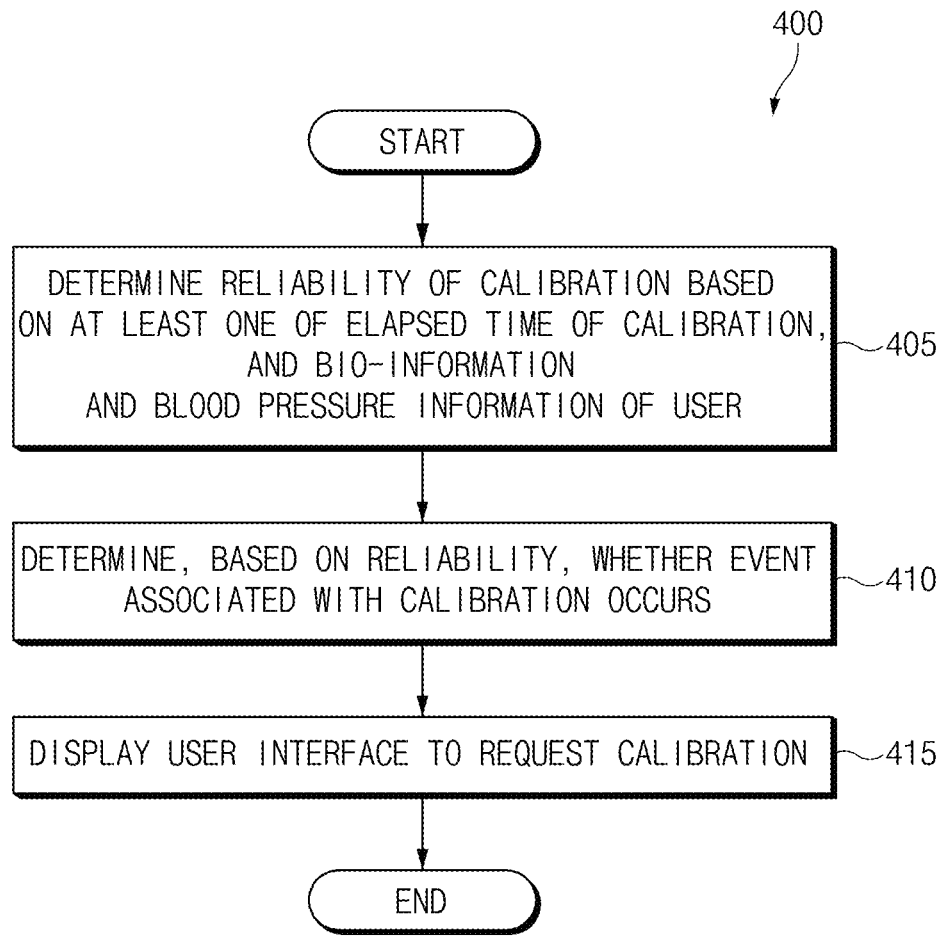
FIG. 4A is a flowchart illustrating the operation of the electronic device requesting calibration based on the reliability of the calibration, according to an embodiment.

FIG. 4A is a flowchart illustrating the operation of the electronic device requesting calibration based on the reliability of the calibration, according to an embodiment. The operations illustrated in FIGS. 4A and 4B may be performed by the electronic device 101 or the processor 220.

Referring to FIG. 4A, in operation 405 of method 400, the processor 220 may determine the reliability of the calibration based on at least one of the elapsed time of the calibration, and the bio-information/blood pressure information of the user measured through the sensor module 240. According to an embodiment, the processor 220 may determine the reliability of the calibration periodically or whenever the user of the electronic device 101 measures his or her blood pressure through the sensor module 240.

For example, the reliability of the calibration may be expressed as following Equation 1.

$$R_i = R_{i-1} - (w_1 \Delta t + w_2 \Delta \text{bio-info} + w_3 \Delta BPV) + b \quad \text{Equation 1}$$

In Equation 1, $R_i$ may refer to the reliability of present calibration (e.g. a second parameter at a second time point) and $R_{i-1}$ may refer to reliability of previous calibration (e.g. a first parameter at a first time point). In addition, $\Delta t$ may refer to elapsed time (e.g. the difference between the first time point and the second time point), $\Delta$bio-info may refer to the variation in bio-information of the user (e.g. the difference in various parameters of the bio-information as compared to that of the previous calibration), $\Delta BPV$ may refer to the variation in blood pressure information of the user as compared to that of the previous calibration, $w_1$ may refer to a weight on $\Delta t$, $w_2$ may refer to a weight on $\Delta$bio-info, $w_3$ may refer to a weight on $\Delta BPV$, and b may refer to bias.

In operation 410, the processor 220 may determine, based on the reliability, whether an event associated with calibration occurs. The event may refer to, for example, the moment that the expiration time point of the calibration comes to pass. In another example, the event may refer to a point in time before the expiration time point of the calibration. For example, if the processor 220 sets the expiration time point of the calibration to 10 days or later based on the reliability, the event may be set to be five days, two days, or one day before the 10 days. In another example, the event may relate to when the electronic device 101 arrives at a preset place or geo-fence. In another example, the event may relate to whether the reliability of the calibration is less than or equal to a specified threshold value and thus the reliability of the calibration enters a different stage, as shown in FIG. 3. The threshold value may include one or more threshold values. For example, the threshold value may refer to boundaries between the stages 310, 320, and 330 illustrated in the graph of FIG. 3.

In operation 415, the processor 220 may display, through the display 260, a UI to request the calibration. For example, the processor 220 may display, through the display 260, the number of days left to the expiration time point of the calibration. The number of left days may be determined based on the current reliability of calibration. According to another embodiment, the processor 220 may notify the user that calibration is required through sound or vibration. According to an embodiment, the processor 220 may increase the frequency of the notification if the expiration time point of the calibration is imminent or has come to pass. According to an embodiment, the processor 220 may request the calibration by displaying, through the display 260, the place associated with the calibration or the geo-fence. The place associated with the calibration may include places such as a hospital, a fitness center, a health center, a gym, or public facilities, i.e. locations where electronic blood pressure monitoring typically takes place. The information on the place associated with the calibration may be previously stored in the memory 230 or may be received by the electronic device from the server. According to an embodiment, if the reliability of the calibration is relatively high, the processor 220 may display the place with a wider radius. But if the reliability of the calibration is relatively low, the processor 220 may prominently display a place associated with calibration registered by the user, a place associated with calibration closest to the current location of the electronic device 101, or a place that the calibration has been performed previously. According to an embodiment, the processor 220 may display the current location of the electronic device 101 along with the place associated with calibration. According to an embodiment, if the electronic device 101 enters a specified place or receives a user input of selecting the specified place, the processor 220 may display the location where blood pressure monitors are held, the number of the blood pressure monitors, waiting time, or the like in a pop-up window. If the electronic device 101 communicates with an electronic blood pressure monitor, the electronic device 101 may display, through the display 260, how to use the electronic blood pressure monitor. A user may measure the blood pressure of the user by using both the electronic device 101 and the electronic blood pressure monitor after a personal authentication procedure of the user is confirmed. The calibration information measured through the electronic blood pressure monitor may be transmitted through a network or may be transmitted through an authenticated cloud server.

According to an embodiment, the processor 220 may display the measured blood pressure through the display 260 after the calibration is performed. According to an embodiment, the processor 220 may display the measured blood pressure together with the reliability of the calibration.

Figure 4B:
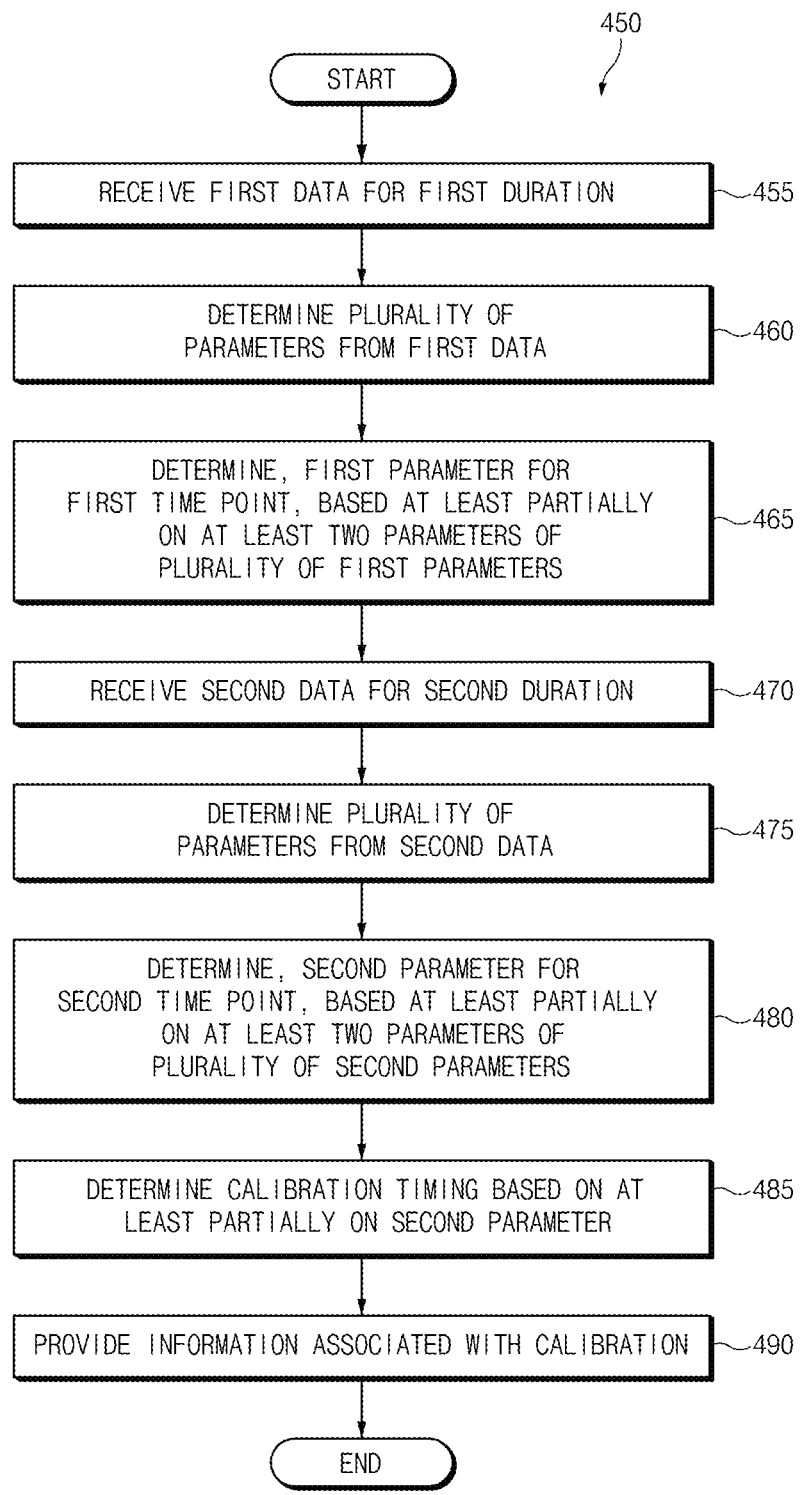
FIG. 4B is a flowchart illustrating the operation of the electronic device to provide information associated with the calibration timing, according to an embodiment.

FIG. 4B is a flowchart illustrating the operation of the electronic device to provide information associated with the calibration timing, according to an embodiment.

Referring to method 450 of FIG. 4B, in operation 455, the processor 220 may receive first data from the sensor module 240 for a specific first duration. According to an embodiment, the processor 220 may receive the first data from the sensor module 240 (e.g., the PPG sensor).

In operation 460, the processor 220 may determine a plurality of parameters based on the first data. According to an embodiment, the plurality of parameters may include at least one of bio-information and blood pressure information (e.g., blood pressure value). The bio-information may include, for example, at least one of information measured through the BIA, stress index, exercise amount, blood sugar, sleep duration, exercise time, heartrate information, and ECG.

In operation 465, the processor 220 may determine a first parameter (e.g., the reliability) for the first time point based at least partially on at least two parameters in the plurality of parameters based on the first data determined in operation 460.

In operation 470, the processor 220 may receive second data from the sensor module 240 for a second duration different from the first duration.

In operation 475, the processor 220 may determine a plurality of parameters based on the second data. According to an embodiment, the plurality of second parameters may include at least one of bio-information and blood pressure information (e.g., blood pressure value). The bio-information may include, for example, at least one of information measured through the BIA, stress index, exercise amount, blood sugar, sleep duration, exercise time, heartrate information, and ECG.

In operation 480, the processor 220 may determine a second parameter (e.g., the reliability) for the second time point based at least partially on at least two parameters in the plurality of parameters based on the second data determined in operation 475. The processor 220 may determine the second parameter according to Equation 1 above.

In operation 485, the processor 220 may determine the calibration timing based at least partially on the second parameter. According to an embodiment, the calibration timing may be expressed as the number of days left until the time of calibration, and the number of the left days may be determined by multiplying a specified duration by the second parameter.

In operation 490, the processor 220 may provide information associated with the calibration timing. For example, the processor 220 may display, through the display 260, information associated with at least one of the blood pressure value and the second parameter.

Figure 5:
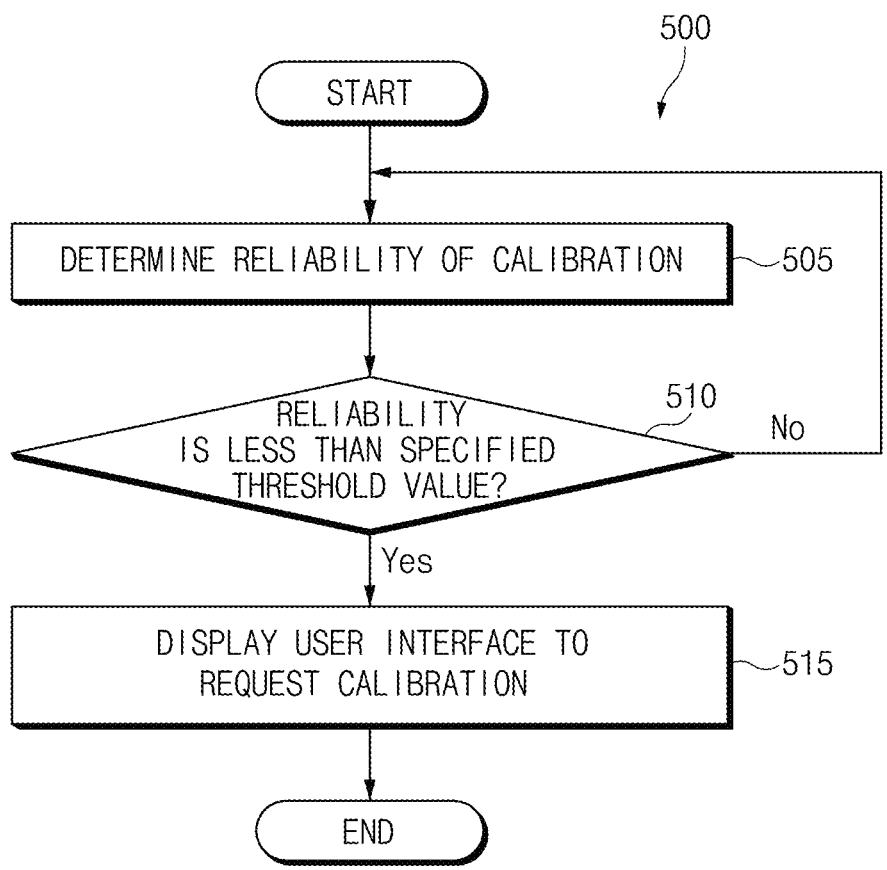
FIG. 5 is a flowchart illustrating the operation of the electronic device to request the calibration based on the reliability of the calibration and a specified threshold value, according to an embodiment.

FIG. 5 is a flowchart illustrating the operation of the electronic device to request the calibration based on the reliability of the calibration and a specified threshold value, according to an embodiment.

Referring to FIG. 5, in operation 505 of method 500, the processor 220 may determine the reliability of the calibration. For example, the processor 220 may determine the reliability of the calibration based on at least one of the bio-information of the user, the elapsed time of the calibration, and the blood pressure information.

In operation 510, the processor 220 may determine whether the determined reliability of the calibration is less than a threshold value. The threshold value may include one or more threshold values. For example, the threshold value may refer to the boundaries between the higher stage 310, the intermediate stage 320, and the lower stage 330 of FIG. 3. According to an embodiment, the threshold value may be variously set depending on the country where the electronic device 101 is in, the performance of the electronic device 101, the performance of the sensor module 240, and the use purpose (e.g., whether the electronic device 101 is dedicated for a medical purpose or a wellness purpose). If the reliability of the calibration is not less than the threshold value, the processor 220 may repeat operation 505 and operation 510. If the reliability of the calibration is less than the specified threshold value, the processor 220 may execute operation 515.

In operation 515, the processor 220 may display the UI to request the calibration through a display or may notify the user of the request through sound or vibration. According to an embodiment, the processor 220 may adaptively display the UI to request the calibration based on the changed reliability of the calibration. For example, since lower reliability of the calibration may indicate that the blood pressure information stored in the electronic device 101 is not accurate, the processor 220 may perform a control operation such that the radius of the geo-fence is increased (with may allow the display of additional blood pressure monitors) or may increase the frequency of the notification for requesting calibration. According to an embodiment, when a camera application or an augmented reality (AR) application is running in the electronic device 101, the processor 220 may display the place associated with the calibration in the form of augmented reality.

Figure 6:
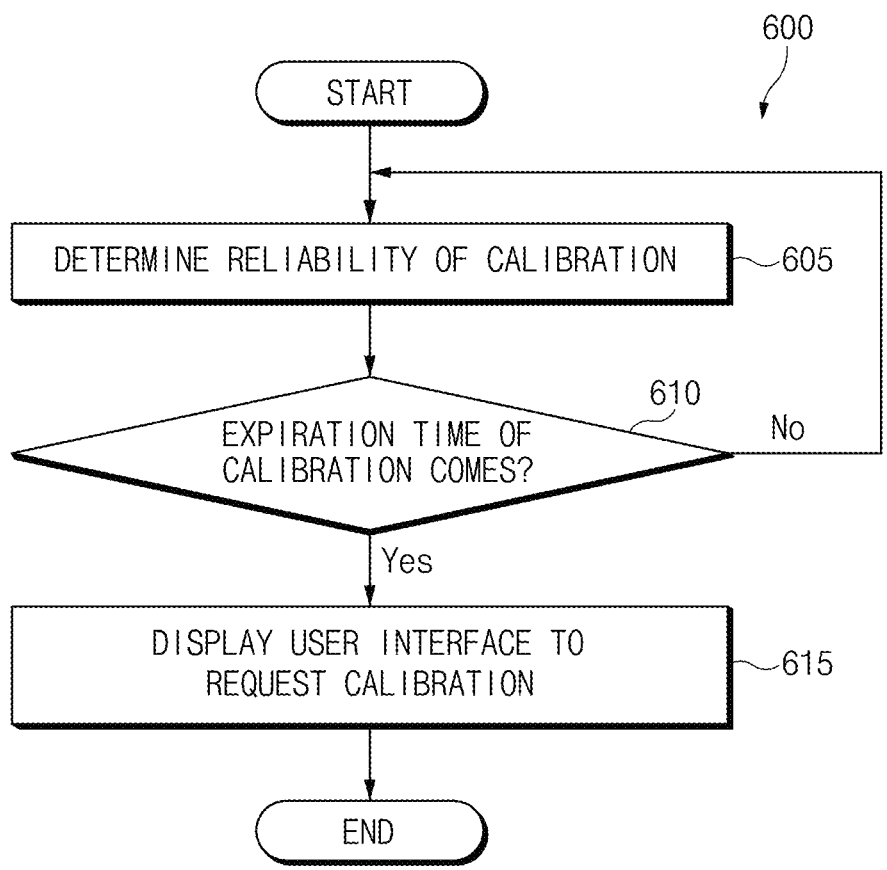
FIG. 6 is a flowchart illustrating the operation of the electronic device to request the calibration based on the expiration time point of the calibration, according to an embodiment.

FIG. 6 is a flowchart illustrating the operation of the electronic device to request the calibration based on the expiration time point of the calibration, according to an embodiment.

Referring to FIG. 6, in operation 605 of method 600, the processor 220 may determine the reliability of the calibration. For example, the processor 220 may determine the reliability of the calibration based on at least one of the bio-information of the user, the elapsed time of the calibration, and the blood pressure information of the user.

In operation 610, the processor 220 may determine whether the expiration time point of the calibration has come to pass. If the expiration time point of the calibration has not come to pass, the processor 220 may repeat operation 605 and operation 610. But if the expiration time point of the calibration has come to pass, the processor 220 may perform operation 615.

In operation 615, the processor 220 may display the UI to request the calibration through a display or may notify the user of the request through sound or vibration. For example, the processor 220 may display a UI showing that the stored blood pressure information is not accurate.

According to an embodiment, since the blood pressure information is not accurate when the expiration time point of the calibration has come to pass, the processor 220 may change a category related to blood pressure information so that the blood pressure information is no longer dedicated for medical purpose bur rather only for wellness purpose.

Figure 7:
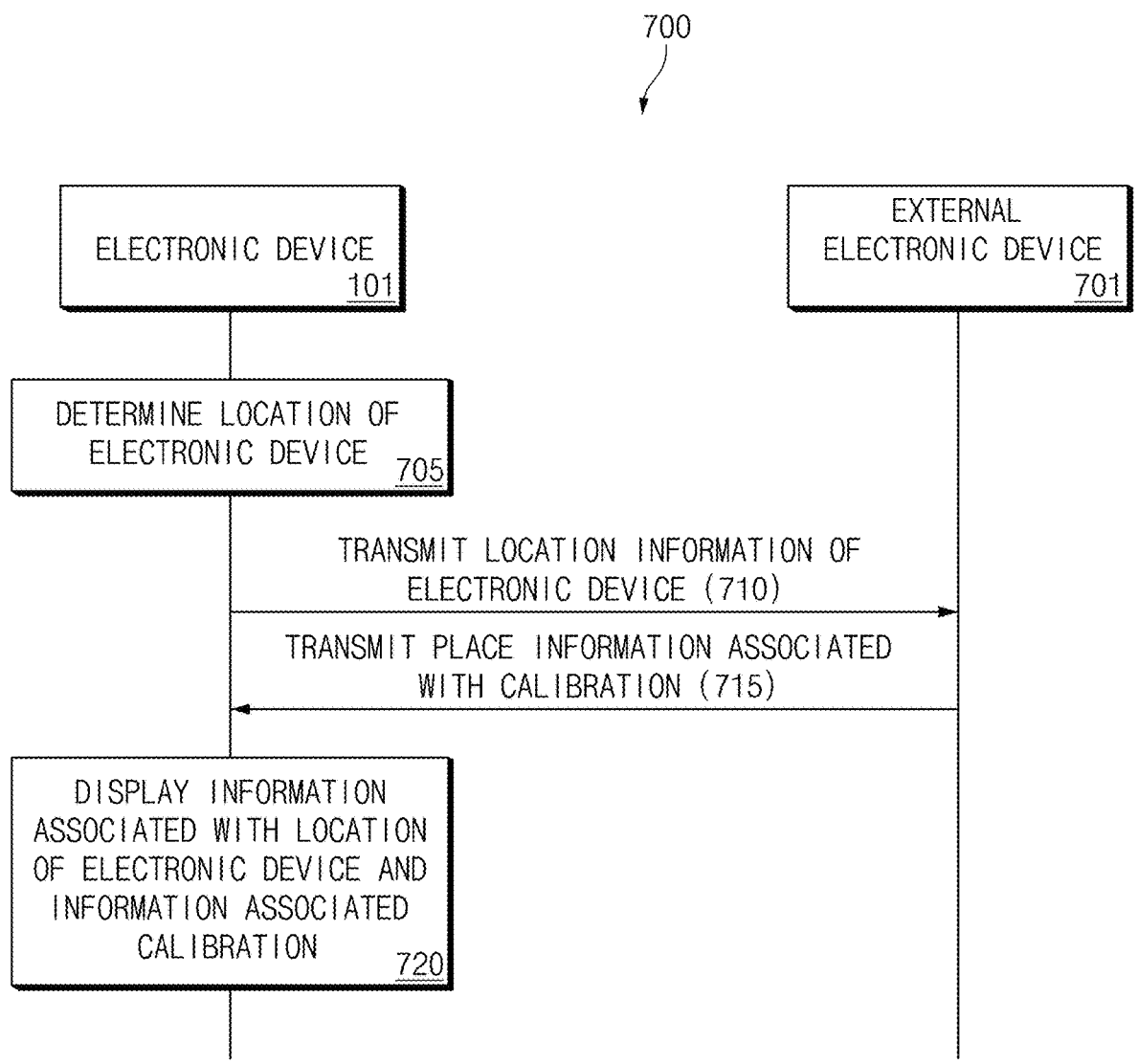
FIG. 7 is a flowchart illustrating the operations of the electronic device and an external electronic device that share place information associated with calibration, according to an embodiment.

FIG. 7 is a flowchart illustrating the operations of the electronic device and an external electronic device that share place information associated with calibration, according to an embodiment. The operations illustrated in FIG. 7 may be operations after the electronic device 101 detects an event associated with the calibration or operations periodically performed by the electronic device 101 regardless of whether the electronic device 101 detects the event.

Referring to FIG. 7, in a network environment 700 (e.g., the network environment 700 of FIG. 1), an external electronic device 701 may be an entity that stores information associated with calibration. For example, the external electronic device 701 may be a smartphone, a tablet, a wearable device, a nearable device, a medical device, or a server.

In operation 705, the electronic device 101 may determine the location of the electronic device 101 through the communication module 290. For example, the electronic device 101 may measure the location of the electronic device 101 through a communication module, such as GPS, WPS, GLONASS, or CPS. In addition, the communication module 290 may be able to measure location through short-range wireless communication modules such as Bluetooth, BLE, WiFi, or NFC. According to an embodiment, the electronic device 101 may change the number of times of determining the location of the electronic device 101, based on the reliability of the calibration. For example, since the lower reliability of the calibration may correspond to the stored blood pressure information being not accurate, the electronic device 101 may increase the number of times of determining the location of the electronic device 101.

In operation 710, the electronic device 101 may transmit the determined location information of the electronic device 101 to the external electronic device 701. According to an embodiment, the location information may include data for requesting place information associated with calibration.

In operation 715, the electronic device 101 may receive the place information associated with the calibration from the external electronic device 701. The place information may include information on a specific place or a geo-fence. The place associated with the calibration may include places such as a hospital, a fitness center, a health center, a gym, or public facilities.

In operation 720, the electronic device 101 may display, through the display 260, the location of the electronic device 101 and the place information associated with the calibration.

Figure 8:
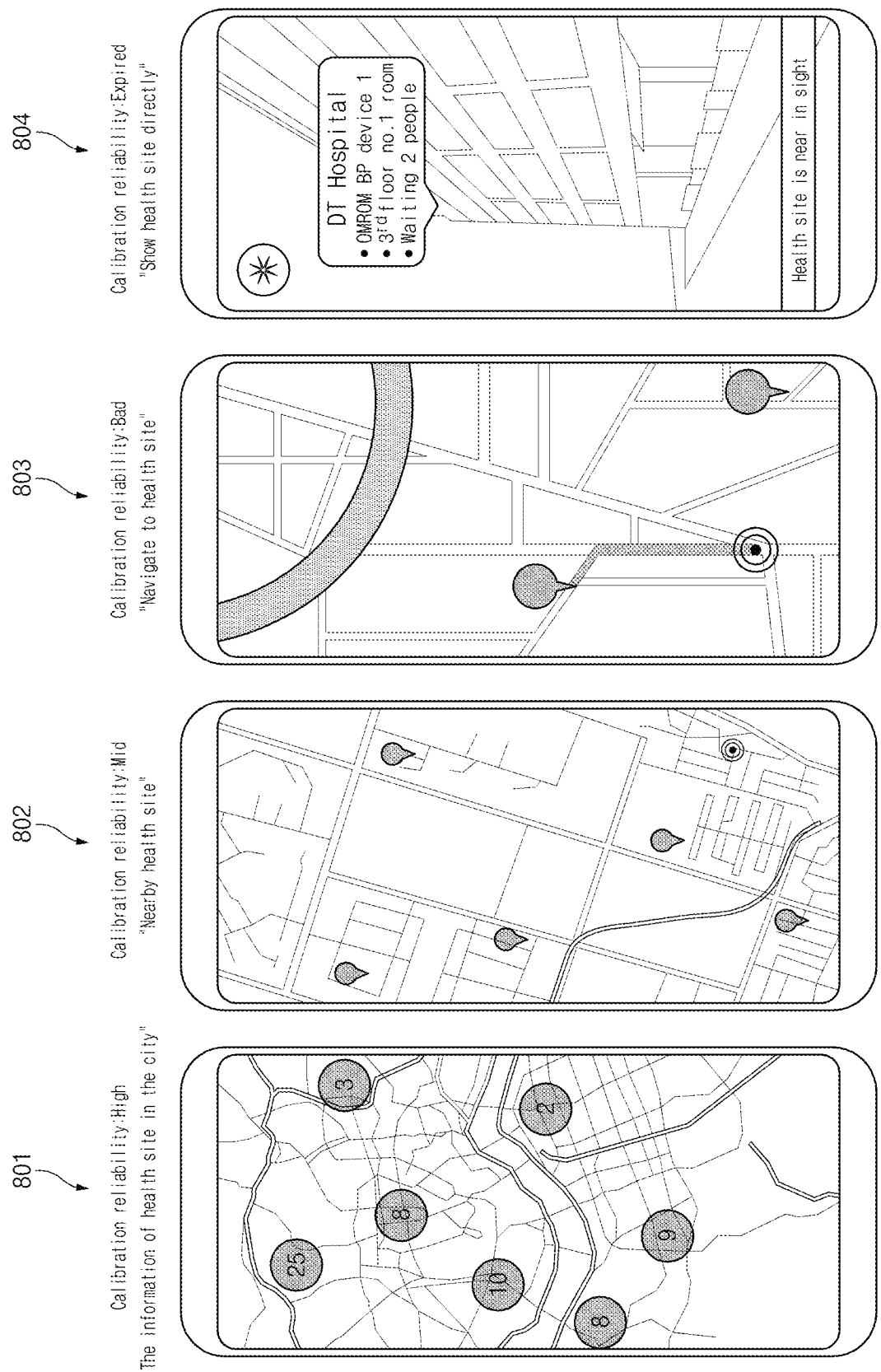
FIG. 8 illustrates a UI to provide the place information associated with the calibration, according to an embodiment.

FIG. 8 illustrates a UI to provide the place information associated with the calibration, according to an embodiment.

Referring to FIG. 8, the electronic device 101 may display the places associated with the calibration differently depending on the stages of the reliability of the calibration. For example, if the reliability of the calibration is relatively high, the electronic device 101 may display the place information on a city scale (e.g. based on a specified radius of 10 km of the electronic device 101) as illustrated in reference numeral 801. In another example, if the reliability of the calibration is in the intermediate stage, the electronic device 101 may display the place information based on a neighborhood scale (e.g. based on a specified radius of 2 km of the electronic device 101) as illustrated reference numeral 802. In another example, if the reliability of the calibration is in the lower stage or if the expiration time point of the calibration has come to pass, the electronic device 101 may display the place information around a specified radius (e.g., 1 km) of the electronic device 101, may display information of a place closest to the electronic device 101, may display a path from the current location of the electronic device 101 to a specified place (e.g., the closest place) as illustrated in reference numeral 803, or may display an image of a specified place as illustrated in reference numeral 804. For example, when a camera application or an AR application is running in the electronic device 101, the processor 220 may display the place associated with the calibration in the form of augmented reality. According to an embodiment, the electronic device 101 may display detailed place information on an image of the specified place, such as the floor number of the place, the number of persons waiting at the place, the devices equipped at the place, etc.

According to an embodiment, the electronic device 101 may display only a subset of places received from the external electronic device 701. For example, the electronic device 101 may recommend a place closest to the electronic device 101 to the user as illustrated in reference numeral 803. For another example, the electronic device 101 may recommend a place located on a path between previously stored places (e.g., home, a workplace, a church, or a school).

Figure 9A:
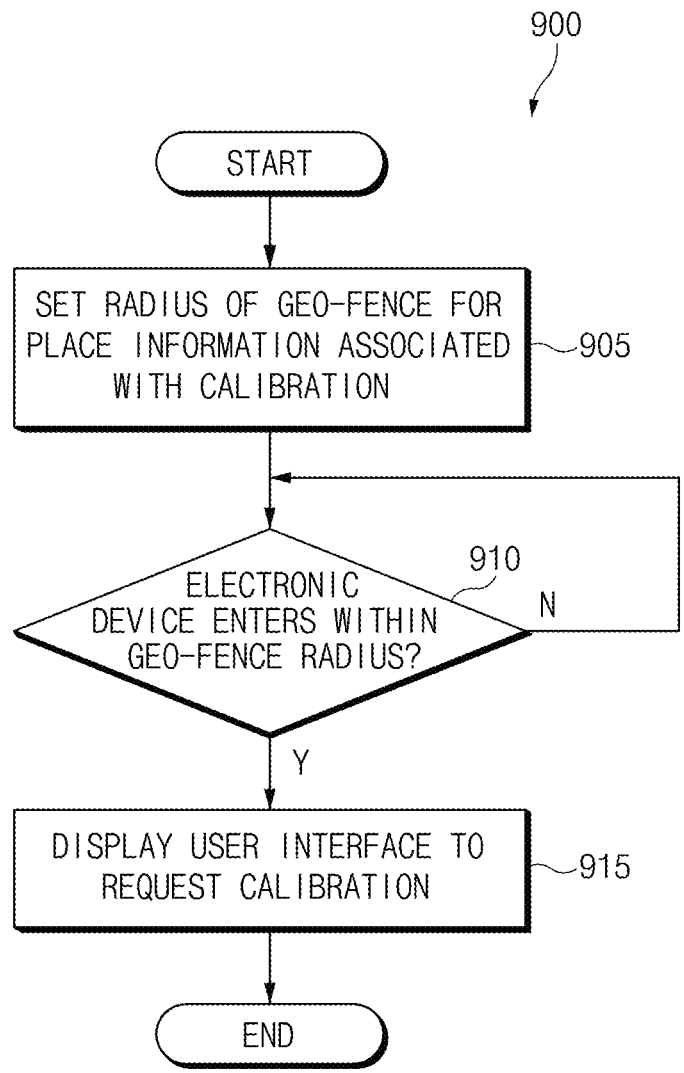
FIG. 9A is a flowchart illustrating the operation of the electronic device to provide the place information associated with the calibration, based on a geo-fence, according to an embodiment.
Figure 9B:
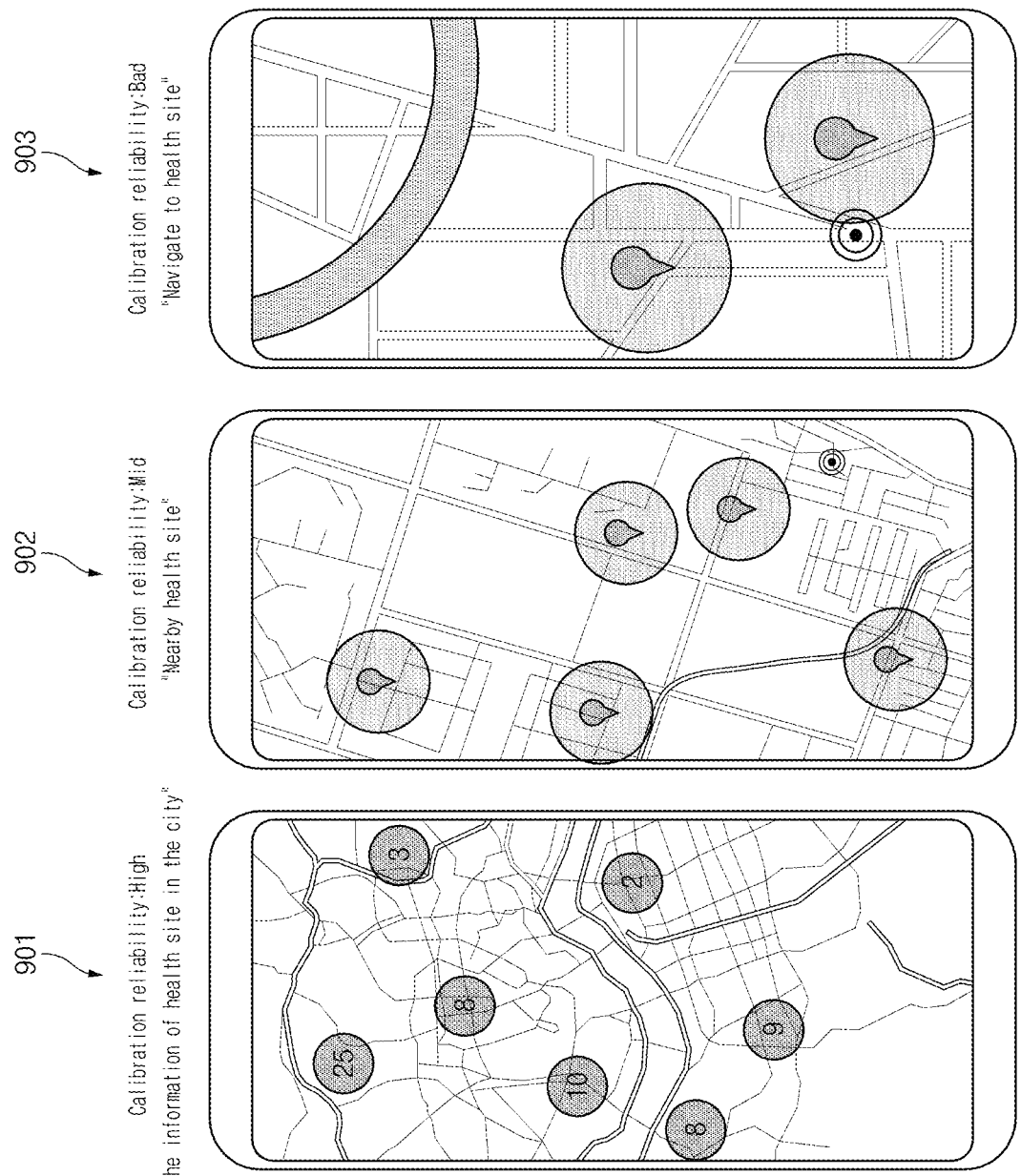
FIG. 9B illustrates an operation of changing the radius of the geo-fence based on the reliability of the calibration, according to an embodiment.

FIGS. 9A and 9B illustrate an embodiment of providing place information associated with calibration based on a geo-fence. FIG. 9A is a flowchart illustrating the operation of the electronic device to provide the place information associated with the calibration, based on a geo-fence; and FIG. 9B illustrates an operation of changing the radius of the geo-fence based on the reliability of the calibration.

Because frequent calibration provides for more accurate blood pressure measurements, the electronic device 101 may request calibration from the user periodically or under a specific condition, even if an event associated with the calibration is not detected. But to prevent the user from being bothered too frequently, the electronic device 101 may request the calibration from the user only when the electronic device 101 is located within a specified geo-fence.

Referring to method 900 of FIG. 9A, in operation 905, the processor 220 may set the radius of a geo-fence for the place information associated with the calibration. For example, the processor 220 may perform operation 905 after receiving the place information from the external electronic device 701 in operation 715 of FIG. 7.

According to an embodiment, the radius of the geo-fence may be changed based on the reliability of the calibration. As the radius of the geo-fence is reduced, the chances of the electronic device 101 being located in the geo-fence is also reduced, and thus the number of times of notifying the user to calibrate blood pressure information is also reduced. In contrast, as the radius of the geo-fence is increased, the number of times of notifying the user to calibrate blood pressure information may increase. For example, referring to FIG. 9B, when the reliability of the calibration is relatively high (e.g. in the higher stage as shown in FIG. 3), the processor 220 may set the radius of the geo-fence to a specified radius (e.g., 10 m) as illustrated in reference numeral 901. When the reliability of the calibration is in the intermediate stage, the processor 220 may set the radius of the geo-fence to a specified radius (e.g., 100 m) as illustrated in reference numeral 902. For another example, when the reliability of the calibration is in the lower stage, the processor 220 may set the radius of the geo-fence to a specified radius (e.g., 1 km) as illustrated in reference numeral 903.

According to an embodiment, the radius of the geo-fence may be determined based on the number of places associated with the calibration. For example, when the electronic device 101 is located in an area, such as an urban area, having the larger number of places associated with the calibration, the processor 220 may set the radius of the geo-fence to be relatively small. In another example, when the electronic device 101 is located in a rural area having a smaller number of places associated with the calibration, the processor 220 may set the radius of the geo-fence to be relatively large.

In operation 910, the processor 220 may determine whether the electronic device 101 enters within the set radius of the geo-fence. If the electronic device 101 does not enter the radius of the geo-fence, the processor 220 may repeatedly perform operation 910 without requesting the calibration.

When the processor 220 detects that the electronic device 101 enters the set geo-fence, the processor 220 may display the UI to request the calibration in operation 915. For example, the processor 220 may display place information associated with the calibration based on the specified radius as illustrated in reference numeral 801 to 803 of FIG. 8. In another example, the processor 220 may display the detailed place information on an image of the specified place, such as the floor number of the place, the number of persons waiting at the place, the devices equipped at the place, etc. as illustrated in reference numeral 804.

Figure 10:
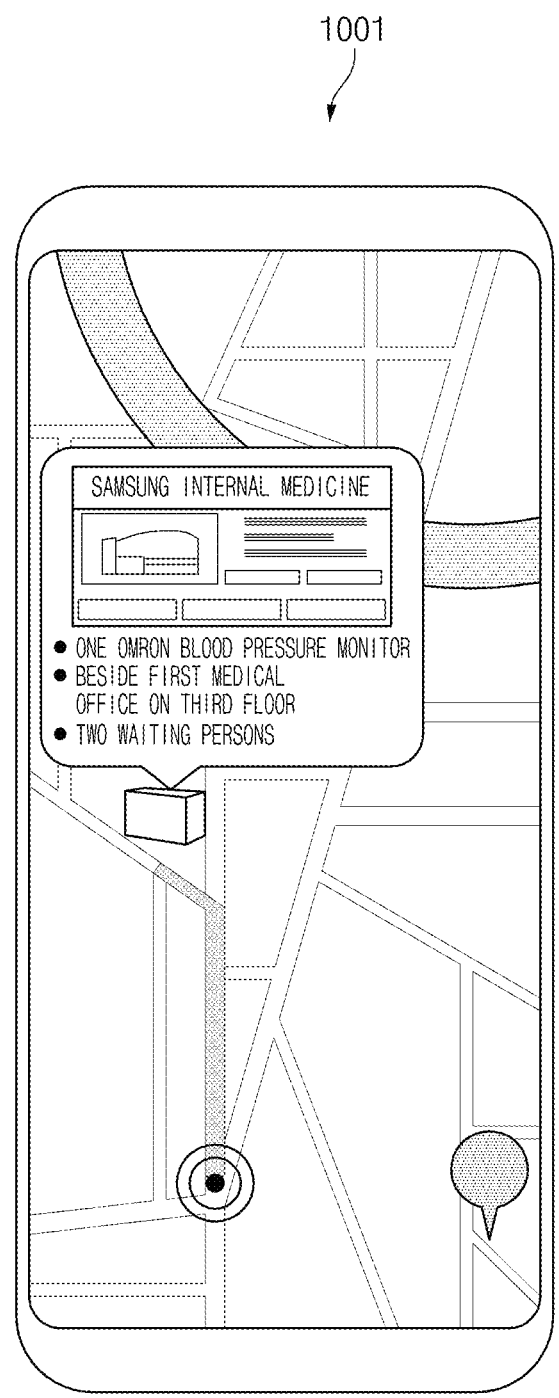
FIG. 10 is a view illustrating a user interface to provide place information associated with calibration in the form of a pop-up window, according to an embodiment.

FIG. 10 is a view illustrating a user interface to provide place information associated with calibration in the form of a pop-up window, according to an embodiment.

Referring to FIG. 10, as the electronic device 101 receives a user input of selecting a specific place or detects that the electronic device 101 enters the specific place as illustrated in reference numeral 1001, the electronic device 101 may display information on the selected place. The information on the place may include, for example, at least one of the types and the number of equipped devices, the name of a place, the number of persons waiting, and phone numbers.

Figure 11:
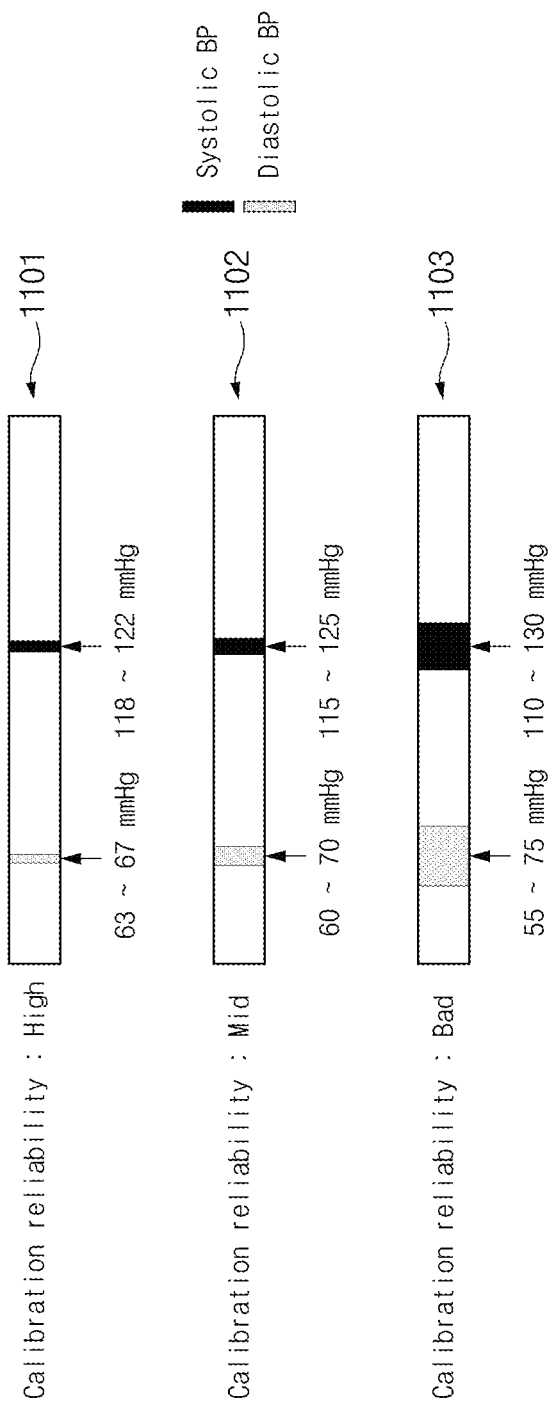
FIG. 11 illustrates a user interface to represent the blood pressure of the user based on the reliability of the calibration, according to an embodiment.

FIG. 11 illustrates a user interface to represent the blood pressure of the user based on the reliability of the calibration, according to an embodiment.

To represent the estimated blood pressure of the user, a higher weight may be applied on the latest (updated) calibration and the influence by information under the previous calibration may be gradually reduced. The estimated blood pressure at almost the expiration time point may be updated using new calibration information. The PPG logging data may be stored in a server for a predetermined period of time.

Referring to FIG. 11, the electronic device 101 may display, through the display 260, the blood pressure value estimated depending on the reliability of the calibration. The blood pressure values may be displayed in terms of systolic blood pressure (SBP), diastolic blood pressure (DBP), or mean arterial pressure (MAP). For example, as illustrated in reference number 1101, when the reliability is in the higher stage, since the estimated blood pressure represents higher accuracy, the electronic device 101 may display the blood pressure value with a narrower reliability section (e.g., 4 mmHg). In addition, since the blood pressure value represents lower reliability as the reliability enters in a lower stage, the electronic device 101 may display a wider reliability section (e.g., 10 mmHg or 20 mmHg) as illustrated in reference number 1102 or reference number 1103.

Figure 12:
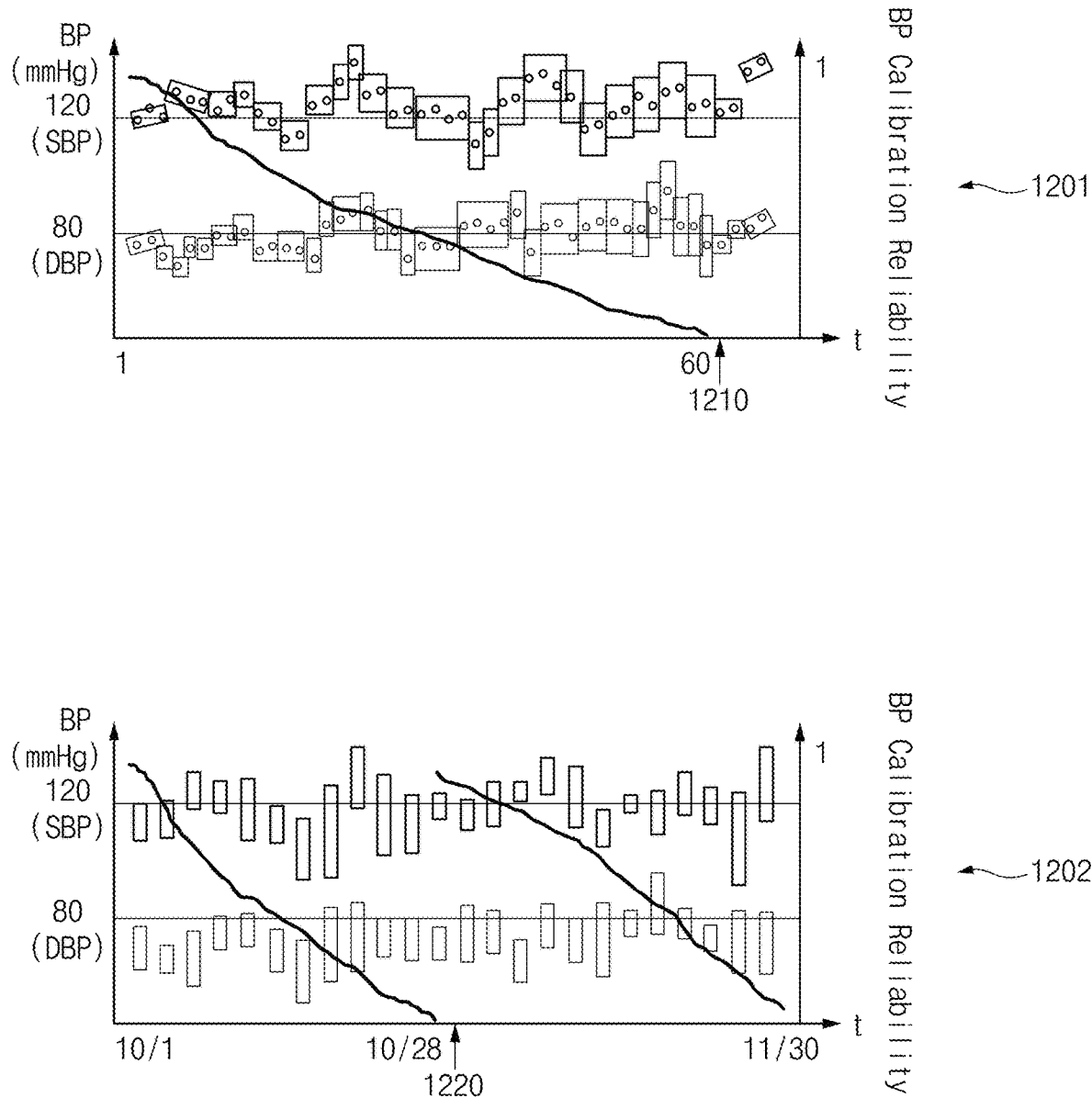
FIG. 12 illustrates another user interface to represent the blood pressure of the user based on the reliability of the calibration, according to an embodiment.

FIG. 12 illustrates another user interface to represent the blood pressure of the user based on the reliability of the calibration, according to an embodiment.

Referring to FIG. 12, the electronic device 101 may display the blood pressure value over time. Graph 1201 may represent blood pressure value determined whenever the electronic device 101 measures the blood pressure. In graph 1201, the horizontal axis may represent time or the number of times that calibration has taken place. Graph 1202 may represent blood pressure values taken on specific days. In graph 1202, the horizontal axis may represent days. In graphs 1201 and 1202, the vertical axis may refer to the reliability of the calibration. The electronic device 101 may represent systolic blood pressure (SBP) and diastolic blood pressure (DBP) along time axes in graph 1201 or graph 1202.

The electronic device 101 may display the reliability section of the measured blood pressure value, based on the reliability of the calibration. For example, in graph 1201, since the reliability of the calibration is degraded over time, the electronic device 101 may display a wider reliability section over time. When the calibration is performed at time 1210, since the reliability is increased, the electronic device 101 may display a narrower reliability section. In another example, in graph 1202, when the reliability is reduced, the electronic device 101 may display the SBP value and the DBP value by relatively blurring the SBP value and the DBP value or displaying them in different colors. When the calibration is performed at timing of reference numeral 1220, since the reliability is increased, the electronic device 101 may revert to the original clarity or color. In addition, the brightness of the reliability sections may also be changed based on the reliability.

As described above, an electronic device (e.g., the electronic device 101 of FIG. 1) may include a sensor module (e.g., the sensor module 240 of FIG. 2), a memory (e.g., the memory 230 of FIG. 2), a display (e.g., the display 260 of FIG. 2), and a processor (e.g., the processor 220 of FIG. 2). The processor may be configured to determine bio-information and blood pressure information of a user measured through the sensor; determine reliability of calibration of the blood pressure information, based on at least one of elapsed time of the calibration, the bio-information, and the blood pressure information, determine, based on the reliability of the calibration, whether an event associated with the calibration occurs, and display a user interface (UI; one of reference numerals 801, 802, 803, and 804 of FIG. 8, or reference numeral 1001 of FIG. 10) to request another calibration, through the display, when the event is determined to have occurred.

According to an embodiment, the processor may be further configured to display the UI to request the other calibration through the display, when the reliability of the calibration is less than a specified threshold value.

According to an embodiment, the specified threshold value may include a plurality of threshold values, and the processor may be further configured to set the plurality of threshold values based on the reliability of the calibration.

According to an embodiment, the processor may be further configured to determine the expiration time point of the calibration, based on the reliability of the calibration, and to display the UI to request the other calibration through the display, when the expiration time point of the calibration comes to pass.

According to an embodiment, the electronic device may further include a communication module (e.g., the communication module 290 of FIG. 2), and the processor may be further configured to measure a location of the electronic device through the communication module, to transmit information on the measured location to an external electronic device (e.g., the external electronic device 701 of FIG. 7), to receive place information related to the other calibration from the external electronic device, and to display the received place information through the display.

According to an embodiment, the processor may be further configured to set a radius for displaying the place information based on the reliability of the calibration.

According to an embodiment, the processor may be further configured to set a radius of a geo-fence around the electronic device based on the reliability of the calibration.

According to an embodiment, the processor may be further configured to display, through the display, the blood pressure information of the user with a reliability section (one of reference numerals 1101, 1102, and 1103 of FIG. 11) for representing the reliability, and to change a color, brightness, and/or a size (e.g., reference numeral 1201 or 1202 of FIG. 12) of the reliability section based on the reliability.

As described above, a method (e.g., method 400 of FIG. 4A) of an electronic device, may include determining bio-information and blood pressure information of a user measured through a sensor of the electronic device, determining reliability of calibration of the blood pressure information, based on at least one of elapsed time of the calibration, the bio-information, and the blood pressure information (e.g., operation 405 of FIG. 4A), determining, based on the reliability of the calibration, whether an event associated with the calibration occurs (e.g., operation 410 of FIG. 4A), and displaying a UI to request another calibration, through a display of the electronic device, when the event is determined to have occurred (e.g., operation 415 of FIG. 4A).

According to an embodiment, the determining of whether the event occurs may include determining whether the reliability of the calibration is less than a specified threshold value (operation 510 of FIG. 5). According to an embodiment, the specified threshold value may include a plurality of threshold values, and the method may further include setting the plurality of threshold values based on the reliability of the calibration.

According to an embodiment, the method may further include determining an expiration time point of the calibration, based on the reliability of the calibration (operation 610 of FIG. 6), and the determining of whether the event occurs may include determining whether the expiration time point of the calibration comes to pass.

According to an embodiment, the method may further include measuring a location of the electronic device (e.g., operation 705 of FIG. 7), transmitting information on the measured location to an external electronic device (e.g., operation 710 of FIG. 7), receiving place information related to the other calibration from the external electronic device (e.g., operation 715 of FIG. 7), and displaying the received place information (operation 720 of FIG. 7).

According to an embodiment, the method may further include setting a radius for displaying the place information based on the reliability of the calibration (e.g., operation 905 of FIG. 9A).

According to an embodiment, the method further include displaying, through the display, the blood pressure information of the user with a reliability section for representing the reliability, and changing a color, brightness, and/or a size of the reliability section based on the reliability.

As described above, an electronic device (e.g., the electronic device 101 of FIG. 1) may include a housing (not illustrated), a touchscreen display (e.g., the display 260 of FIG. 2) exposed through a first part of the housing, a photoplethysmogram (PPG) sensor (e.g., the sensor module 240) exposed through a second part of the housing and configured to make contact with a portion of a user's body such that blood pressure of the user is measured, a wireless communication circuit (e.g., the communication module 290 of FIG. 2) disposed inside the housing, a processor (e.g., the processor 220 of FIG. 2) disposed inside the housing and operatively connected with the touchscreen display, the PPG sensor, and the wireless communication circuit, and a memory (e.g., the memory 230 of FIG. 2) disposed inside the housing, operatively connected with the processor, and storing instructions. When executed, the instructions may cause the processor to receive first data from the PPG sensor for a first duration, to determine a first plurality of parameters from the first data, to determine a first parameter for a first time point, based at least partially on at least two parameters in the first plurality of parameters, to receive second data from the PPG sensor for a second duration, to determine a second plurality of parameters from the second data, to determine a second parameter for a second time point, based at least partially on at least two parameters in the second plurality of parameters, to determine calibration timing based at least partially on the second parameter, and to display information associated with the calibration timing on the touchscreen display.

According to an embodiment, the first plurality of parameters and the second plurality of parameters may include at least two or more of information measured through a bio-electrical impedance analyzer (BIA), a stress index, an exercise amount, blood sugar, a sleep duration, exercise time, heartbeat rate information, and a blood pressure value.

According to an embodiment, the first parameter is expressed as $R_{i-1}$, the second parameter is expressed as $R_i$, and relationship between the first parameter and the second parameter is expressed through Equation 1.

According to an embodiment, the calibration timing may be expressed as a number of days left until a calibration is required, and the number of the days left may be determined by multiplying a specified duration by $R_i$.

According to an embodiment, the instructions may further cause the processor to display, on the touchscreen display, information associated with at least one the blood pressure value and the second parameter.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "$1^{st}$" and "$2^{nd}$," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

What is claimed is:

1. An electronic device comprising:
   a sensor;
   a memory;
   a display; and
   a processor,
   wherein the processor is configured to:
      determine bio-information and blood pressure information of a user measured through the sensor;
      determine reliability of a first calibration of the blood pressure information, based on at least one of elapsed time of the first calibration, the bio-information, and the blood pressure information;

determine, based on the reliability of the first calibration, whether an event associated with the first calibration occurs;

display a user interface (UI) to request a second calibration, through the display, when the event is determined to have occurred, display a place information associated with the second calibration on a city scale if the reliability of the first calibration is in a higher stage, display the place information on a neighborhood scale if the reliability of the first calibration is in an intermediate stage, and display a closest place from the electronic device associated with the second calibration or display a path from a current location of the electronic device to the closest place if the reliability of the first calibration is in a lower stage or if an expiration time point has come to pass, wherein the expiration time point is a point when the reliability of the first calibration becomes zero.

2. The electronic device of claim 1, wherein the processor is further configured to:
display the UI to request the second calibration through the display, when the reliability of the first calibration is less than a specified threshold value.

3. The electronic device of claim 2, wherein the specified threshold value includes a plurality of threshold values, and wherein the processor is further configured to:
set the plurality of threshold values based on the reliability of the first calibration.

4. The electronic device of claim 1, wherein the processor is further configured to:
determine the expiration time point of the first calibration, based on the reliability of the first calibration; and
display the UI to request the second calibration through the display, when the expiration time point of the first calibration comes to pass.

5. The electronic device of claim 1, further comprising:
a communication module,
wherein the processor is further configured to:
measure a location of the electronic device through the communication module;
transmit information on the measured location to an external electronic device;
receive the place information related to the second calibration from the external electronic device; and
display the received place information through the display.

6. The electronic device of claim 5, wherein the processor is further configured to:
set a radius for displaying the place information based on the reliability of the first calibration.

7. The electronic device of claim 5, wherein the processor is further configured to:
set a radius of a geo-fence around the electronic device based on the reliability of the first calibration.

8. The electronic device of claim 1, wherein the processor is further configured to:
display, through the display, the blood pressure information of the user with a reliability section for representing the reliability; and
change a color, brightness, and/or a size of the reliability section based on the reliability.

9. The electronic device of claim 1, wherein the reliability of the first calibration is expressed through Equation 1, $$R_i = R_{i-1} - (w_1 \Delta t + w_2 \Delta \text{bio-info} + w_3 \Delta BPV) + b, \text{and} \qquad \text{Equation 1}$$

wherein $R_i$ refers to a reliability of a present calibration, $R_{i-1}$ refers to a reliability of a previous calibration, $\Delta t$ refers to a difference between a first time point corresponding to $R_{i-1}$ and a second time point corresponding to $R_i$, $w_1$ refers to a weight applied to $\Delta t$, $\Delta$bio-info refers to a variation in the bio-information, $w_2$ refers to a weight applied to the $\Delta$bio-info, $\Delta BPV$ refers to a variation in the blood pressure information, $w_3$ refers to a weight applied to the $\Delta BPV$, and b refers to a bias.

* * * * *